United States Patent

Spier

[11] Patent Number: 6,005,159
[45] Date of Patent: *Dec. 21, 1999

[54] PROTECTIVE COVERING FOR BODY LESIONS

[75] Inventor: I. Martin Spier, New York, N.Y.

[73] Assignees: Alan J. Ackerman, East Brunswick, N.J.; Leonard Cooper, Palham Manor, N.Y.

[ * ] Notice: This patent is subject to a terminal disclaimer.

[21] Appl. No.: 09/175,279

[22] Filed: Oct. 20, 1998

Related U.S. Application Data

[63] Continuation of application No. 08/757,105, Dec. 2, 1996, abandoned, which is a continuation-in-part of application No. 08/390,642, Feb. 17, 1995, Pat. No. 5,580,346.

[51] Int. Cl.⁶ ........................................................ A61F 5/00
[52] U.S. Cl. ................................ 602/42; 602/54; 128/888
[58] Field of Search ....................... 602/41–54; 128/888, 128/889

[56] References Cited

U.S. PATENT DOCUMENTS

| | | |
|---|---|---|
| 3,950,483 | 4/1976 | Spier . |
| 4,399,816 | 8/1983 | Spangler . |
| 4,641,643 | 2/1987 | Greer .................................... 602/57 X |
| 4,865,026 | 9/1989 | Barrett . |
| 4,909,243 | 3/1990 | Frank ........................................ 602/42 |
| 5,086,763 | 2/1992 | Hathman ................................. 602/42 |
| 5,106,362 | 4/1992 | Gilman ..................................... 602/47 |

*Primary Examiner*—Richard J. Apley
*Assistant Examiner*—Kim M. Lee
*Attorney, Agent, or Firm*—Leonard Cooper

[57] ABSTRACT

A protective covering for a lesion comprises a frame for adhering to the skin of a patient and for surrounding a lesion. The frame has a central opening and a generally L-shaped cross section including a wall, and a base that surrounds the lesion and attaches to the patient's skin with an adhesive. One end of the wall extends perpendicularly from the base, extending around the central opening. The free end of the wall includes a peripheral recess wherein a rim of a cover is received. The cover aligns with the opening and the rim extends fully around the cover so that when the frame base is attached to the patient's skin surrounding a lesion, and the rim of the cover is sealingly received in the recess of the wall, a sealed space is provided enclosing the lesion to protect it from the water. The cover may be put on and taken off the frame many times while the adhesive connection between the frame and skin remains intact. Tabs on the frame allow for tugging the frame in opposition to locally applied forces as the cover rim is pressed into the recess of the frame.

18 Claims, 4 Drawing Sheets

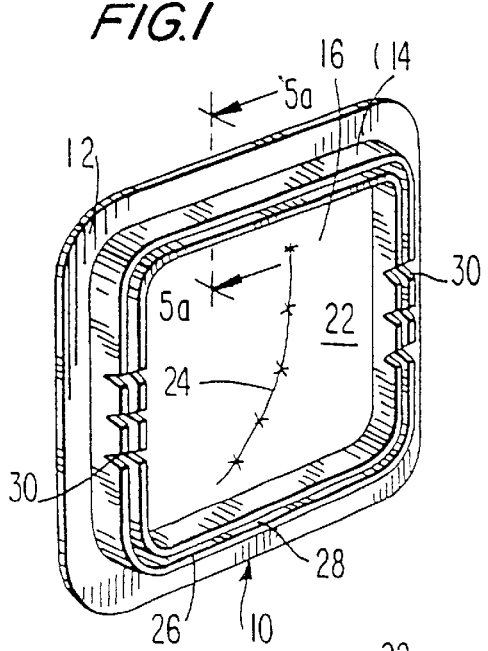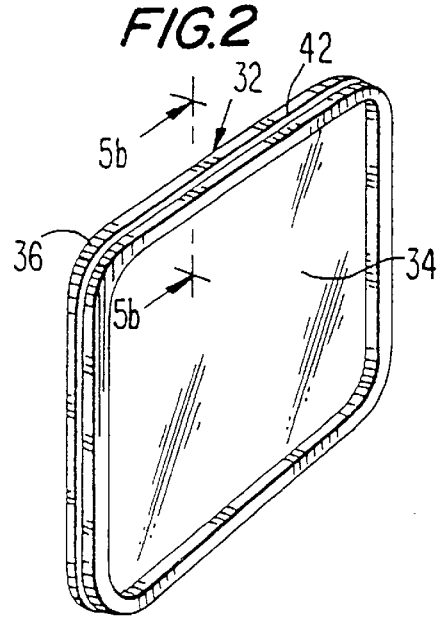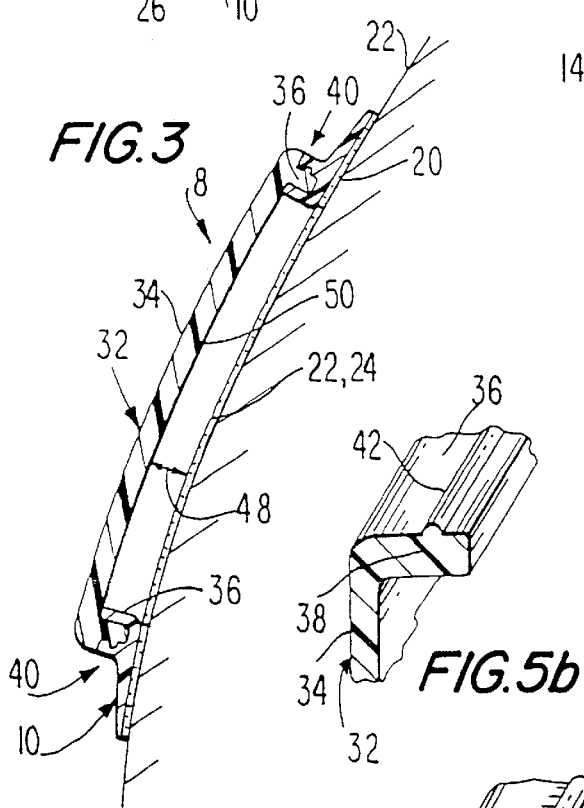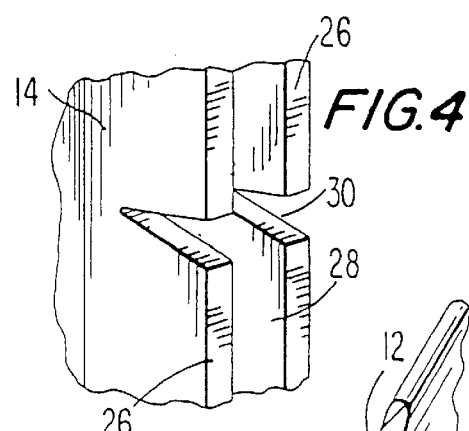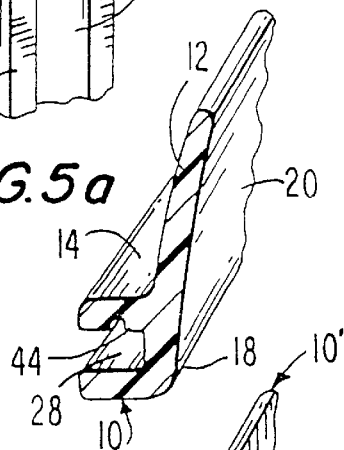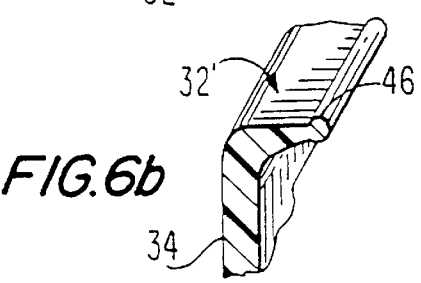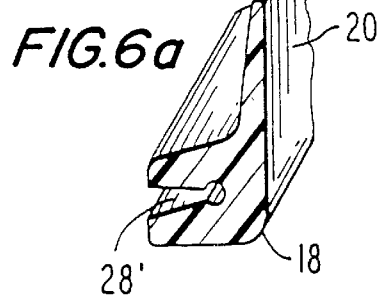

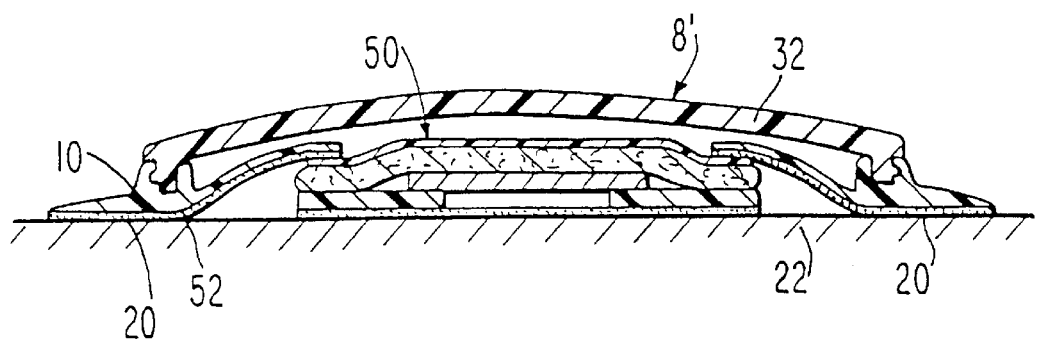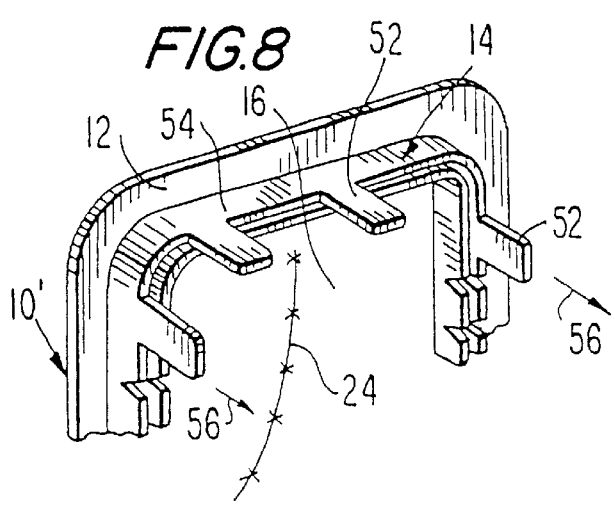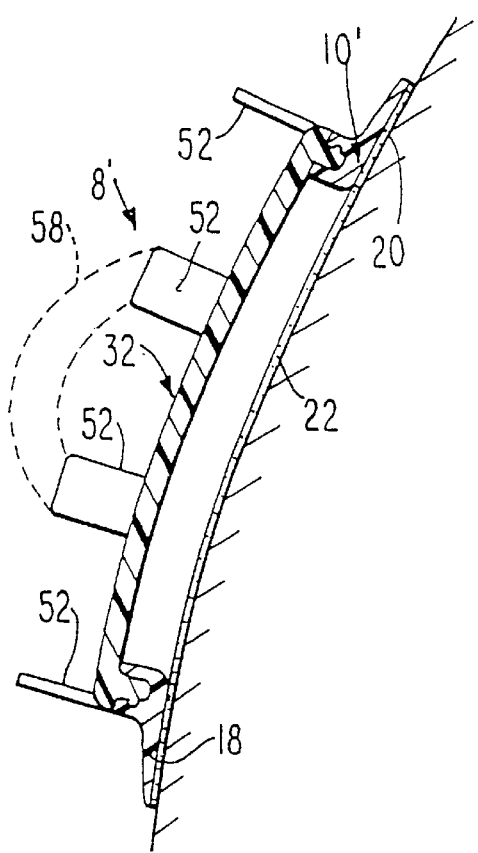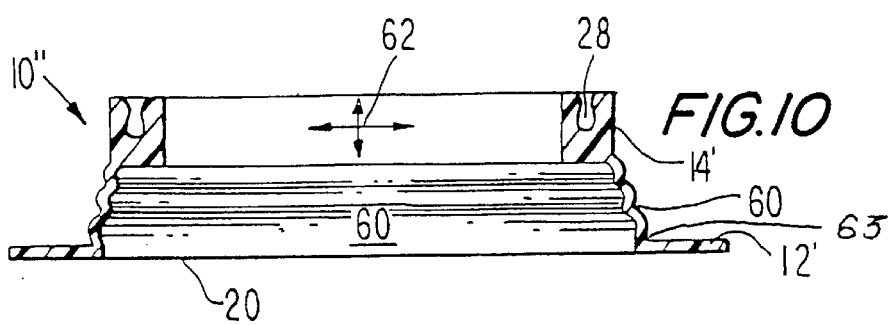

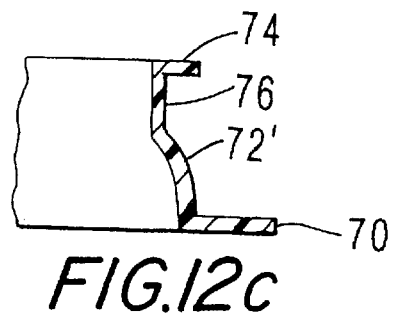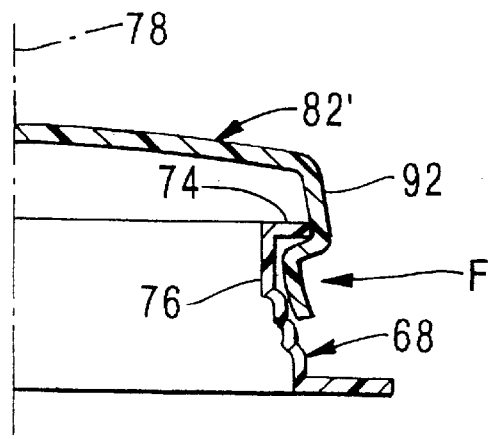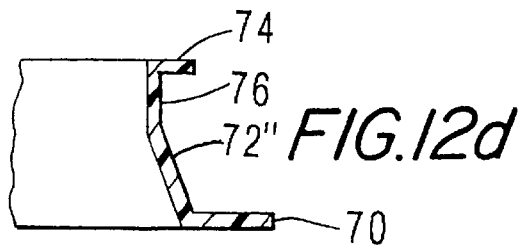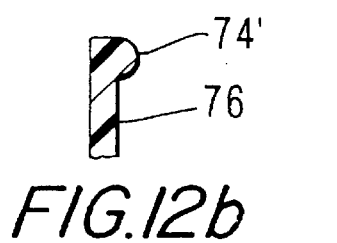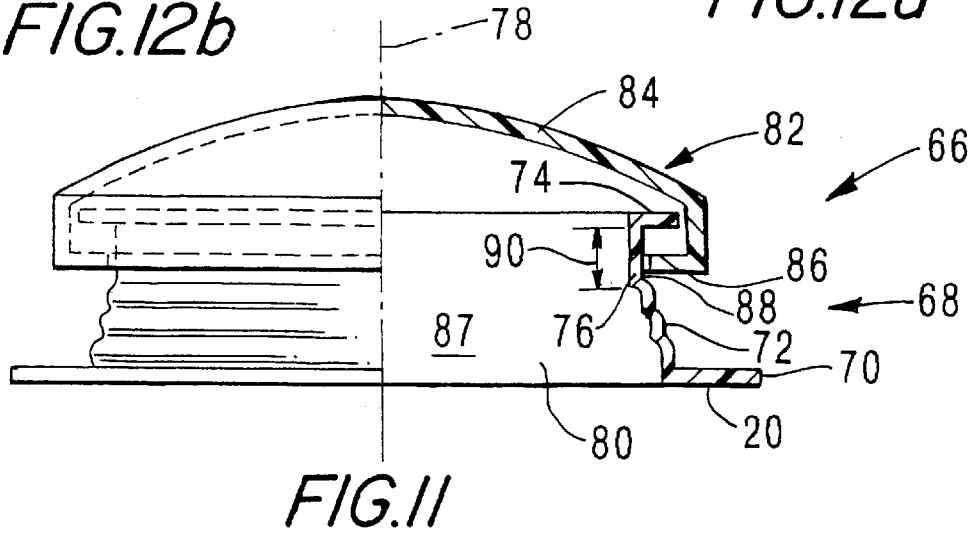

PROTECTIVE COVERING FOR BODY LESIONS

This is a continuation of 08/757,105, filed Dec. 2, 1996 (abandoned), which is a continuation-in-part of Ser. No. 08/390,642, filed Feb. 17, 1995, now U.S. Pat. No. 5,580,346.

BACKGROUND OF THE INVENTION

This invention relates generally to a protective covering for a body lesion, and more particularly, to a protective covering for a lesion during bathing and showering by the wearer. Whereas there is a constant stream of new developments related to medical cures, disease detection and protection, magnetic resonance imaging, gene splicing, etc., some of the more prosaic and basic problems that have haunted medical practice through its annals, go unattended and without advancement to keep pace with other events.

When a person has a body lesion, whether that lesion is in the process of healing or that lesion is intended to be a permanent or semi-permanent part of the anatomy so as to substitute for a bodily function or to assist in medical treatments or procedures, a problem is created when the patient must be bathed by emersion in a tub or by taking a shower. Also, people having lesions may wish to exercise by swimming, whether for therapy or general conditioning. To this day, some of the finest, modem medical facilities in the world, when facing the problem of bathing or showering, offer a film of thin plastic, which is more commonly used in the kitchen to wrap leftover food, as a protective sheathing to be wrapped to cover a lesion in the hope that water will not reach the affected area.

A wound that is covered with padding and gauzes, perhaps containing medication, can be adversely affected by contact with water, scabs may dissolve and impede the process of healing, and the danger of infection is increased at the wound site. Another approach to protecting a lesion during bathing or showering, is to cover the lesion with a bandage that is taped around the edges and to completely cover the lesion. However, it is known that removing adhesive bandages from close proximity to a wound often aggravates the skin near the lesion causing sensitivity, swelling, hazards of infection, and loss of skin where the adhesive is removed. Thus, such bandaging techniques have disadvantage when bathing and have not been widely used in recent years.

A similar problem arises with regard to adhesive bandages when using these adhesives to hold pads, and the like, in place to provide protection for the lesion and also frequently to apply medication or provide drainage means.

For these reasons, treatment devices include a frame or base having a central opening. The base includes an adhesive surface and is positioned so that the opening surrounds the body lesion when the base is attached to the body surface (skin). Wound dressing materials are then placed over the lesion by passing them through the opening in the base. These dressing materials are attached to the base and may be removed and changed without the need for removing the base from the skin surface. Thus, the problem of wound and skin irritation that results from repetitive addition and removal of adhesive tape to the skin, is avoided.

U.S. Pat. No. 5,106,362, issued Apr. 21, 1992, to Gilman discloses a dressing for a wound including a vent which provides controlled leakage of fluid from the wound along a path through an opening in a base sheet or frame of the device, which is attached to the skin using an adhesive. In this device, the frame need not be removed each time the dressing is changed. The device is primarily intended to control the outflow of fluid oozing from a wound and prevention of bacterial infection of the wound is also a problem which is considered.

U.S. Pat. No. 4,865,026, issued Sep. 12, 1989, is a sealing/wound closure device which includes an annular ring that is attached to the skin with an adhesive. A closure device for drawing the edges of a wound together operates through the central opening of the ring or frame that is attached to the skin. A removable cover is placed over the closure device. This cover may be removed such that medications may be changed, etc. without disturbing the adhesive connection between the frame and skin.

U.S. Pat. No. 5,086,763, issued Feb. 11, 1992, to Hathman provides a protective recloseable wound dressing. The dressing is disposable and the device has a hinged flap arrangement whereby it is easy to gain access to the wound without disturbing a protective crust of blood and serum that forms over a wound. In addition, it is easy to apply medication without removing the bandage which is attached by adhesive to the skin surrounding the wound. Ready access to the lesion is provided through the hinged opening mechanism. The device may be repeatedly opened for inspection or for application of medication and thereafter be reclosed, without losing the integrity of the seal on the body or on the hinged flap.

U.S. Pat. No. 4,909,243, issued Mar. 20, 1990, is for a wound dressing system that also includes a frame with a central opening that is permanently attached to the skin. A pad of a desired wound dressing material is placed over the frame with the dressing material opposite the wound. The pad is held to the frame by an adhesive having less holding power than the adhesive which keeps the frame on the skin. A patent to Spangler, U.S. Pat. No. 4,399,816, issued Aug. 23, 1983, is similar to U.S. Pat. No. 4,909,243. In Spangler, the pad is placed in the central opening of a frame and is covered by a hinged cover that is permanently attached at one edge to the frame. Thus, the cover can be raised and lowered so that there is access to the wound and any padding that is placed thereon.

Each of the patents addresses the problems that arise from frequent removal of adhesive material from the skin in the immediate vicinity of a wound. However, none of the patents addresses the problem of bathing or showering or discloses a covering for the wound that not only protects the wound during such activity but avoids the aforementioned irritation associated with frequent removal of adhesive bandages, and the like, from the wound vicinity.

What is needed, is a protective covering for body lesions that is simple to use and effective in preventing contamination of a wound or lesion, and its dressing or medication, by exposure to water during bathing, showering, therapeutic baths, exercise, and the like.

SUMMARY OF THE INVENTION

Accordingly, it is an object of the invention to provide an improved protective covering for body lesions that prevents access to the wound by liquids during baths and showers, and the like.

Another object of the invention is to provide an improved protective covering for body lesions that addresses the problem associated with frequent addition and removal of adhesive material to the skin adjacent a wound.

Yet another object of the invention is to provide an improved protective covering for body lesions that can be used in conjunction with prior art devices that hold medications and dressings in place over a wound.

Still another object of the invention is to provide an improved protective covering for body lesions that is simple to use, protects a lesion from exposure to liquids, and is readily adaptable and non-interferring with regard to other treatments, examinations, or use of a lesion on the body surface.

Still another object of the invention is to provide an improved protective covering for body lesions wherein the cover can be added and removed without excessive pressures or pulling on the body surface, and an extremely effective water seal is made by the cover. A protective covering for a lesion in accordance with the invention comprises a frame for adhering to the skin of a patient and for surrounding a lesion. The frame has a central opening and a generally L-shaped cross section including a wall, and a base that surrounds the lesion and attaches to the patient's skin with an adhesive. One end of the wall extends perpendicularly from the base, extending around the central opening. The free end of the wall includes a peripheral recess wherein a rim of a cover is received.

The cover aligns with the opening and the rim extends fully around the cover so that when the frame base is attached to the patient's skin surrounding a lesion, and the rim of the cover is sealingly received in the recess of the wall, a sealed space is provided enclosing the lesion to protect it from water.

Curved protective coverings may be provided, and elastic covers may be "snapped" into place.

The cover may be put on and taken off the frame many times while the adhesive connection between the frame and skin remains intact.

Tabs on the frame allow for tugging the frame in opposition to locally applied forces as the cover rim is pressed into the recess of the frame.

The invention accordingly comprises the features of construction, combinations of elements and arrangements of parts which will be exemplified in the constructions hereinafter set forth, and the scope of the invention will be indicated in the claims

BRIEF DESCRIPTION OF THE DRAWINGS

For a fuller understanding of the invention, reference is had to the following description taken in connection with the accompanying drawings, in which:

FIG. 1 is a front perspective view of a main element or frame of a protective covering for body lesions in accordance with the invention;

FIG. 2 is a cover used in conjunction with the element of FIG. 1 in accordance with the invention;

FIG. 3 is a sectional view of a protective covering for body lesions in accordance with the invention showing an assembly of the elements of FIGS. 1 and 2;

FIG. 4 is an enlarged portion of the frame of FIG. 1;

FIG. 5a is an enlarged view taken along the line aye 5a—5a of FIG. 1, and FIG. 5b is an enlarged view taken along the line 5b—5b of FIG. 2;

FIGS. 6a and 6b are views similar to FIGS. 5a,b of an alternative embodiment in accordance with the invention;

FIG. 7 is a partial sectional view of another alternative embodiment of a protective covering, in accordance with the invention FIG. 8 is a fragmented view similar to FIG. 1 of yet another alternative embodiment of a protective cover for body lesions in accordance with the invention;

FIG. 9 is a view similar to FIG. 3 of the embodiment of FIG. 8;

FIG. 10 is a front elevational view, in section, of an alternative embodiment of a protective covering, in accordance with the invention;

FIG. 11 is a front elevational view, in partial section, of another alternative embodiment of a protective covering, in accordance with the invention;

FIGS. 12a–d are modifications of the embodiment of FIG. 11;

FIG. 13 is a partial front elevational view, in section, of yet another alternative embodiment of a protective covering, in accordance with the invention.

DESCRIPTION OF PREFERRED EMBODIMENTS

Figure 14:
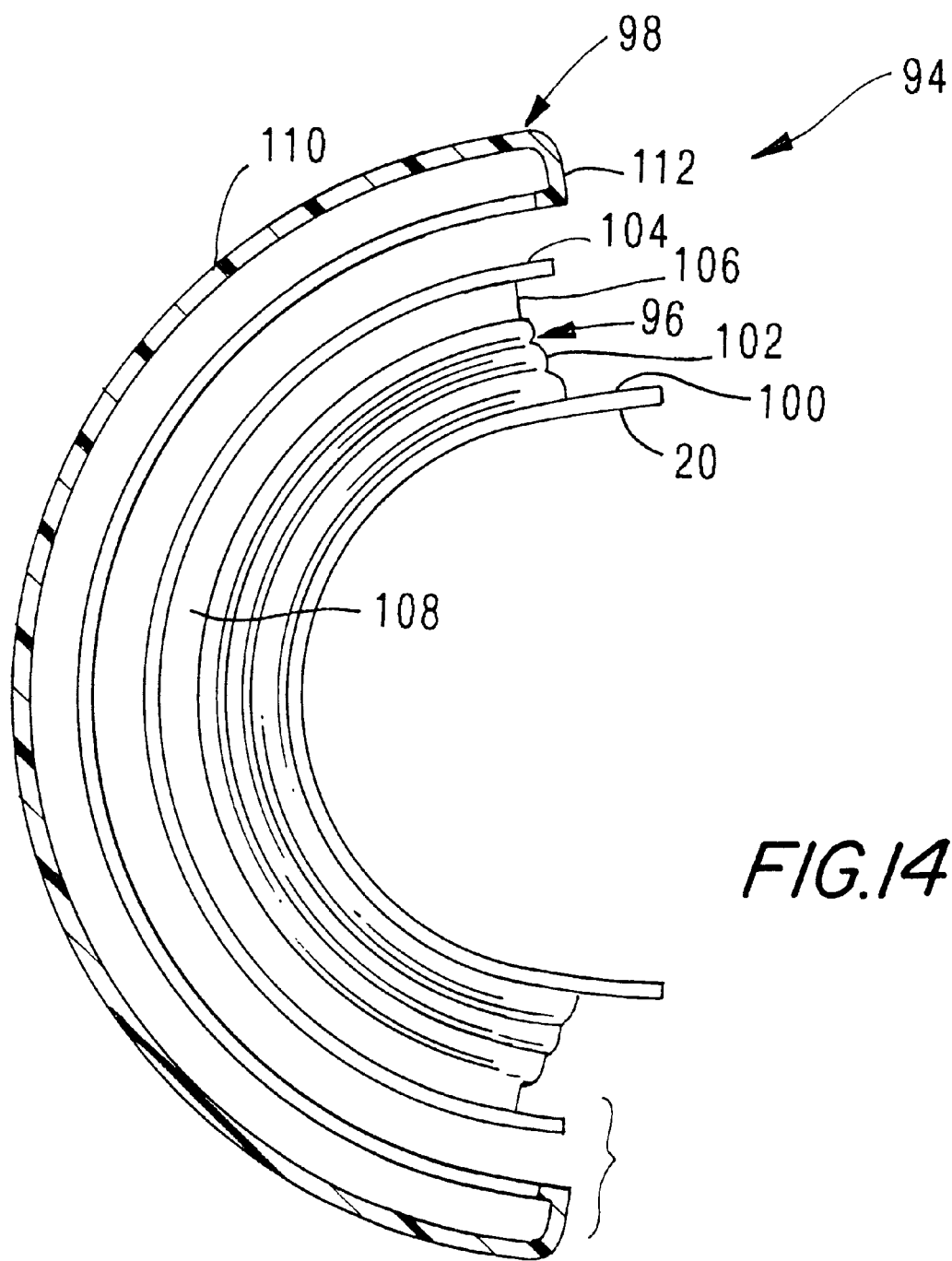
FIG. 14 is a front elevational view, partially in section, of still another alternative embodiment of a protective covering, in accordance with the invention.

With reference to FIGS. 1–6b, a protective covering 8 for body lesions in accordance with the invention includes a frame 10 having a generally planar rectangular base 12 with a rectangular opening 16 defined in the base. A wall 14 rises from the base 12 at the periphery of the opening 16. The base 12 and vertical wall 14 are formed integrally of a flexible plastic material, for example, polyethylene, polyurethane, and polypropylene, and a surface 18 (FIG. 5a) of the base 12 has a thin adhesive layer 20 whereby the frame may be attached to the skin 22 of a person and surround a lesion 24 of the skin. Such skin adhesives are known in the art. The base 12 is bendable to permit attachment on curved body surfaces.

The free edge 26 of the wall 14 has a recess or socket 28 formed therein extending toward the base 12. The entire frame 10 is flexible and this flexibility is enhanced by V-shaped notches 30 cut into the walls of the socket 28, that is, cut into the vertical wall 14. FIG. 1 and FIG. 4 illustrate such notches 30 cut into two opposite parallel segments of the wall 14; notches 30 can also be provided on the other wall segments. The notches help to assure that the frame 10 readily bends to match the user's body contours and a water tight seal is made by the adhesive 20 with the skin 22 around the entire periphery of the frame 10, in use. The frame 10, with or without the notches 30, assures the desired complete sealing contact, and the frame can be made in many sizes and in shapes other than rectangular; e.g., round, oval, as suits the location and type of lesion which is to be protected.

A cover 32 for use with the frame 10 includes a rectangular panel 34 similar in size and in shape to the opening 16 in the frame 10. The panel 34 is of transparent plastic as illustrated, but is not so limited. At the periphery of the cover, a rectangular rim 36 extends generally at a right angle to the panel 34. The rim 36 has a perimeter and cross-section 38 that is contoured to fit sealingly within the recess or socket 28 of the frame 10 when the cover 32 is seated in position on the frame 10 (FIG. 3). In the sealed condition, a water-tight connection 40 is made between the frame 10 and cover 32 that extends around the entire periphery of the frame and cover. When the cover is sealed, a watertight enclosure is made over the skin 22 and lesion 24 as a result of the complete adhesive seal 20, the sealed joint 40 between the mated rim 36 and socket 28, and the watertight integrity of the cover wherein the panel 34 is made integral with the rim 36.

Such a sealed connection as illustrated in FIGS. 3 and 5a, b is well known in the art and is readily made from available plastic materials such as polyethylene, polyurethane, and polypropylene.

In FIGS. 5a,b, the tightness of the joint 40 is enhanced by an O-ring type element 42 that is made as an integral part of the cover 32. The O-ring type element 42 has greater resiliency than the plastic in the other portions of the protective covering 10.

Fabrication of plastic elements having portions of different resiliency is also well known in the art, for example, as described in U.S. Pat. No. 3,950,483, issued Apr. 13, 1976, by the inventor here, and incorporated herein by reference.

A peripheral groove 44 formed in the socket 28 receives the O-ring type element 42 when the connection is made between the frame 10 and cover 32. This added feature provides additional protection against moisture seepage through the joint 40 and also increases the resistance to unintended separation of the cover from the frame 10.

FIGS. 6a,b show an alternative embodiment of a joint 40' wherein a knob 46 is formed at the free end of the cover 32' and the socket 28' is contoured to receive the knob 46. The knob 46 may be of the same flexibility as the remainder of the frame 32' or may be more resilient.

FIG. 3 is a cross-section through a protective covering 8 for a body lesion in accordance with the invention illustrating the frame 10 attached by adhesive 20 to the skin 22 of a person. The frame 10 surrounds a lesion 24 of the skin 22. The cover 32 is illustrated sealingly connected to the frame 10 in a construction of the joint 40 corresponding to FIGS. 5a,b. A clearance 48 is left between the skin 22 and the inner surface 50 of the panel 34.

In manufacture, protective coverings 8 can be made not only with different peripheral outlines but also with different amounts of clearance 48. Thus, the device, when properly selected, can be used over lesions that are covered with other bandages, pads, medications, etc.

As illustrated in FIG. 7, the protective covering 8' in accordance with the invention, can be placed over and surround a conventional dressing 50 of another type that is applied to the lesion. (For the sake of an example in FIG. 7, a dressing similar to FIG. 3 in U.S. Pat. No. 5,106,362, issued Apr. 21, 1992, has been illustrated.) In all embodiments, the same reference numerals as in the earlier figures are used for similar parts. Conventional use can be made of the dressing 50 when the cover 32 is not attached.

In using a protective covering 8' in accordance with the invention, the frame 10 is adhered to the skin 22 of the person, using the adhesive 20 to make a complete seal. As stated, the frame 10 is positioned to surround the other device 50 that has a border 52 adhered to the skin 22 of the user. As illustrated in FIG. 7, the border 52 of the patent device 50 is integral with the frame 10, although the frame 10 may be entirely separate from the device 50.

In using a covering 8, 8', after the frame 10 is in place on the skin, the cover 32 can be pressed into place by mating the rim 36 in the socket 28 of the frame 10 whenever a hazard arises that the lesion may become wet. Such a hazard occurs at times of bathing, showering, swimming, etc.

After the hazard that may cause wetting of the wound has ended, it is only necessary to separate the cover 32 from the frame 10 until the next need arises. The adhesive 20 and the frame 10 remain in position on the skin 22 for extended periods of time, and for many cycles of use of the protective covering 8 for body lesions in accordance with the invention.

A problem may arise when the protective covering is used over lesions where pressing the cover 32 in place causes discomfort and pain. In order to alleviate this discomfort, in an alternative embodiment in accordance with the invention (FIG. 8), a frame 10', which is substantially similar to the frame 10 of FIG. 1, is provided. Tabs 52 extend from the outer lip or surface 54 of the vertical wall 14 and extend away from the base 12. The tabs 52 are flexible and lack rigidity. These tabs 52 are formed or made integral with the vertical wall 14 and are spaced around the periphery of the opening 16. When a person is applying the cover 32 to the frame 10', he or she grasps the tab 52 adjacent to the immediate area where the rim 36 is being applied to the frame 10', and a slight outward pulling with constant force, as indicated by the arrow 56, is applied to the tab 52. The pulling force on the tab 52 is not such that would stress the adhesive connection 20 to the skin 22 but is a counter-force to the local force of pressing insertion of the rim 36 of the cover 32 at that area. As the rim is inserted at different portions of the periphery of the opening 16, the nearest tab 52 (or tabs) is pulled gently with the constant force. The force applied to the tabs 52 counteracts the force applied by the cover at the point of connection, and relieves the pressure on the skin 22 itself. Thus, discomfort, if any, in applying the cover to the frame can be substantially relieved or eliminated.

Such tabs may be used on other devices of a similar nature that are adhered on the skin of a person in the vicinity of a lesion and have a moving part, whether for protection or for application of medication, etc.

Additionally, adjacent tabs 52, in an alternative embodiment, may be joined together at their ends so as to form a loop, as indicated with broken lines 58 in FIG. 9, which a person can more easily grip so as to apply the outward force in the direction 56, as needed. Additionally, the spacing of the tabs 52 around the opening 16 can be different in different applications and the tabs may be closely placed to substantially curtain the periphery, if not the entire periphery of the opening. As stated, the tabs, or the curtain formed to serve a similar function, are of extremely low rigidity and thus, although permanent on the frame 10', do not cause an interference that might otherwise be an obstacle to other devices and procedures related to the lesion.

A tab or tabs may also be part of the cover 32 so that these tabs (not shown) may be pulled in removing the cover 32 from the frame 10 after bathing, showering, etc. Such tabs on the cover 32 would be positioned so as not to interfere with the tabs 52 on the frame.

FIG. 10 illustrates a frame 10" including a base 12' with an adhesive coating 20 around its perimeter for attachment to the skin of a patient. The central opening 16 of the base 12' is surrounded by a wall 14' that is separated from the base by a web 60. The web 60 is resilient so that the wall 14' may be moved in any direction as illustrated by the crossed two-headed arrows 62. The web 60 is sealed (63) to the base 12' around the entire periphery of the opening 16 and is joined sealingly to the wall 14' so that when a cover 32 is mated with the wall 14' by connection, as described above, in the recess socket 28, an enlarged enclosure about a lesion may be provided.

The web 60 may be completely without rigidity such that the wall 14' can be placed anywhere in relation to the base 12' within the physical limits of the web length between the frame and wall. On the other hand, the web may have a degree of resilience with memory in the nature of bellows (FIG. 10) that tend to keep the wall 14' separated from the base 12' when no forces are applied to the wall 14', but still allow movement of one relative to the other. Movement of the wall can then be in any direction toward, away from, and transversely relative to base 12. Flexibility in the web 60 also allows for bending of the base 12' without loss of the seal between the frame 10' and a cover.

In FIG. 10, the opening in the wall 14' is smaller than the opening in the base 12'. Alternatively, the opening in the wall portion may be larger (not shown) than the opening in the base portion. When a force is applied to the wall 14' in the direction toward the base 12', the web 60 can bend, pivoting about or near the web/base joint 63. The web 14' can be wavy in cross section, as in FIG. 10, or may be arcuate (FIG. 12c), convex or concave, or substantially linear (FIG. 12d) between the base and wall. The length of the web 60 between the base 12' and the wall 14' is at least twice the thickness of the web 60 and preferably in a range of 4 to 8 times the thickness to facilitate the bending at or near the joint 63.

By having the resilient web 60 between the wall 14' and the base 12', forces applied to the wall 14', for example, when attaching the cover 32, are not directly transmitted to the wearer's skin in the area of the lesion as in the case of the embodiment of FIG. 1. In actual use, any snagging of the cover 32 does not immediately stress the adhesive 20 or transmit forces to the skin.

Also, when applying the cover 32, the wall 14' can be held between the fingers while the rim 36 is pressed into the recess or socket 28. Thus, no force is transmitted to the skin. In removing the cover 32, the wall 14' can be held between the fingers while the cover 32 is pried off the wall 14'.

In every embodiment, the elements are impervious to water, at least in the direction from the outside of the device toward the patient's skin. However, it should be understood that for all of the embodiments described above, the constructions need not be made leak-tight. The cover 32 may be permeable to gases, such as air, and may include, for example, a grid or pattern of openings, or combinations of such features. The joint between the cover and frame need not be leak-tight.

Such a covering would be used as a lesion protector although one not especially suited for water immersion. The cover may hold in place bandages, dressings, medications, and the like, against the lesion during treatment and healing. These items may be attached to the cover, and may be used and then discarded along with the cover, while the frame remains attached to the skin.

The cover can also be made of a material that can be be punctured by a syringe and be self-healing when the syringe needle is withdrawn, whereby a wound covered by a lesion protector in accordance with the invention, can have medication added and removed, or washing solutions can be added and removed, etc., without destroying the leak-tight characteristics of the protector.

As previously stated, the protective covering can have different shapes to suit different portions of the body, for example, generally round, oval, rectangular, and others. Particular shapes designed for special body regions can be provided. For example, a frame can be constructed for connection to the face for protection of an eye. The frame may attach adhesively near the eyebrow location, extend down along the side of the person's face and onto the cheekbone region. The shape would finish with contact along the side of the nose.

The embodiments of FIGS. 1–10 illustrate a cover/frame connection of the male/female type. Whereas this connection can be very effective in preventing leakage, it is costly to make in comparison with other connections that are available.

Basically, any connection that is now in use for covering containers, for example, orange juice bottles, or temporary plastic caps that are put onto metal containers after the containers have been opened, or covers as used on 8 ounce "tubs" of margarine, can be used. These cover/body connections may be generally categorized as telescopic fits, where generally the cover member slides over and around the container member, using assorted bulges and interferences to assure tight retention of the cover on the container. All such connections between cover and body are applicable in the present invention, and are considered to be within the scope of the invention although not novel, per se. In a situation where the general container outline is circular, the cover may be threaded onto the frame, where proper mating threads are provided on the elements.

In an alternative embodiment (FIG. 11) of a protective covering 66 in accordance with the invention, a frame 68 includes a circular base 70 that can attach to the surface of a user's skin using an adhesive 20. A web 72 connects to a radially extending closure flange 74 by means of a generally cylindrical wall 76. The frame 68 is symmetrical about the axis 78, although as in the previous embodiments, many other shapes are available including rectangles, ovals, and the like. Special shapes of the opening 80 may also be provided, for example, around the eye socket.

A cover 82 includes a panel 84 and a generally radially inwardly extending rim 86. The cover 82 may be clear or opaque and may be domed as illustrated, or it can be generally planar in extending over the frame 68 so as to provide an enclosed space 87 over a lesion (not shown). The inward radial edge 88 of the rim 86 slides on the cylindrical wall 76 of the frame 68 to provide a water-tight seal when the cover is applied to the frame. The web 72 may be wavy, linear, or arcuate, and as described above with regard to bending and pivoting.

The illustrated cover and frame (FIG. 11) provide a line of contact between the cover and frame at the edge 88, which is basically defined by the thickness of the rim 86. In variations (FIG. 12a) the edge 88' is spread for greater contact and may have small peripheral flutes (not shown). Also, the cover may be made of a material having elastic properties such that there is a compressive force acting between the edges 88, 88', and the outer cylindrical surface 76 on the frame 68 to enhance leak-tightness. Slight stretching of the cover would be required when attaching the cover to the frame. A suitable material having desirable elastic properties is thermoplastic rubber, for example, Santoprene, a trademark of Monsanto Chemical Company.

When the protective cover 66 is applied to a curved portion of the user's body, the cover, whether merely resilient or whether elastically resilient, tends to slide at the edge 88, 88' on the surface of the cylindrical wall 76 so as to adapt for the bending in the overall device. The seal is maintained regardless of the bending. Accordingly, the cylindrical wall 76 provides a great advantage where the protective covering 66 is used on a curved body surface or there is movement of a user's body that changes the surface contours during actual usage of the device. The length 90 of the wall 76 in the direction of the axis 78 can be selected in manufacture in consideration of the intended location of use for the device 66 on the person's body. Where more bending is expected, a greater length 90 is advantageous to assure that the cover will not separate from the frame and permit leakage.

It should be appreciated that FIGS. 11 and 12a–d are not drawn to scale, but are drawn to illustrate the concepts of the invention. In this regard, the closure flange 74 of FIG. 11 may be replaced with another protrusion, for example, a hemispherical bead 74' that extends around the frame 68 (FIG. 12b).

The embodiments of FIGS. 11 and 12a–d provide an effective protective device at a lower cost than the embodiments illustrated in FIGS. 1–10.

FIG. 13 is another alternative embodiment in accordance with the invention. The frame 68 is substantially the same as in FIG. 11. However, the cover 82' is a simple sleeve with one end closed (a cup) that is made of a resilient elastic material. The sleeve 92 may be "snapped" over the closure flange 74 (or other protrusion) and may be held there by its own elasticity when the cover 82' is made of, for example, rubber or rubber-like material of a quality as in a party balloon or a condom. Alternatively, a force can be applied to the outside periphery of the sleeve 92 as indicated by the arrow F so as to press the cover 82' against the wall 76 of the frame 68. This force could be applied by a simple rubber band (not shown) that encircles the assembly.

Thus, a less costly embodiment than the embodiments previously described is provided.

Alternatively and in accordance with the invention, the cover (not shown) to be used with the frame 68 could be a simple flexible plastic sheet, for example, Saran Wrap, that is laid onto the frame 68 and held in place with a rubber band loop that presses the cover against the wall 76 of the frame 68. In each of these embodiments, the cover is inexpensive to fabricate and can be disposed after each use, or retained for reuse.

In embodiments where compressive force holds the cover to the frame, the flange 74 or other protrusion may be omitted.

In the above embodiments, it is presumed that the adhesive surfaces 20 are generally planar as manufactured. They may be curved when applied to the body or during use after application to the body. Because it is known that in many instances a protective covering will be required on a curved body surface, for example, on the arms and legs, an alternative embodiment in accordance with the invention is fabricated with a frame and a cover that are already curved, and retain the curvature when not applied to the user's body.

In the protective covering 94, a curved frame 96 is combined (FIG. 14) with a curved cover 98. A generally U-shape is illustrated although the angle of the bend can be less than 180 degrees. The frame 96 includes a curved base 100 connected to a web 102, here illustrated as wavy, although it may have generally planar or arcuate surfaces. The web 102 connects to the closure flange 104 (or other protrusion) by means of a cylindrical wall 106. In this instance, the word "cylindrical" indicates that the distance around the frame 96 on the wall or collar 106 is substantially equal at all distances from the flange 104. Thus, the cover will fit tightly against the surface 106 regardless of its exact location on the surface.

The cover includes a panel 110 that may be opaque or transparent and an inwardly turning rim 112 that encircles the entire periphery.

Both the frame 96 and cover 98 are made of the resilient materials, as described above. The cover may also have elastic properties such that when snapped onto the frame 96 there is a compressive connection between the rim 112 and the collar 106 of the frame 96. Features as discussed in relationship to FIGS. 12a,b and 13 can also be applied to the frame 96 of FIG. 14.

Generally speaking, the curvature, which is provided in the elements of the embodiment in FIG. 14, is less than the curvature of the body area where the protective device 94 is to be applied. Thus, the device is made with resilient materials in the frame 96, and the cover may be resilient or resilient with elasticity, to adapt to the actual body contours.

As all plastic materials (and metals) have elasticity in an engineering sense, it should be understood that "elasticity" is used in this application to indicate an ability to stretch by finger grip force and then to return to original shape after the stretching force is removed. Thus, the elastic features that are used with the present invention are visibly apparent upon application of force and do not refer to the properties of elasticity as might be present in a metal bar, and requiring thousands of psi to produce small elongations.

Also, it should be noted that different materials and properties may be used for the frame and the cover. The frame may be resilient but not elastic in that it is not readily stretchable. The cover may be resilient, or resilient and elastic in that it is stretchable with hand force. The frame can also have resilient as well as elastic properties and both the frame and the cover may use the same material and properties. Also, the frame can be of one material and the cover of another material.

Further, as stated with regard to the embodiments of FIGS. 1–10, the cover need not provide a water tight seal. The cover may be constructed, for example, to provide ventilation and the device may be designed to provide ventilation whether through the cover or through the side surfaces of the frame. In these instances, the ready access to the lesion and the resilient and/or elastic properties of the elements provide substantial advantages. The resilient or elastic properties allow the frame to flex and absorb shocks and forces and rubbing by objects, e.g., blankets, etc., without direct transmission of forces to the skin at the adhesive joint 20. Without an attached cover, the frame still provides a degree of protection of a lesion from physical abuse.

It will thus be seen that the objects set forth above, among those made apparent from the preceding description, are efficiently attained, and since certain changes may be made in the constructions set forth above without departing from the spirit and scope of the invention, it is intended that all matters contained in the above description and shown in the accompanying drawings shall be interpreted as illustrative and not in a limiting sense.

What is claimed is:

1. A protective covering for a body lesion of a patient, comprising:

a frame having a base with a base surface, said base surface having adhesive means for maintaining said frame in sealed contact with a body surface of said patient, said frame defining an opening for surrounding said lesion;

a cover for covering said frame opening, a continuous joint being formed around said opening between said frame and said cover, an enclosed space being produced over said lesion when said cover connects to said frame at said joint and said frame is in said contact with said body surface;

connection means on said frame and cover for forming said joint and releasably joining said cover to said frame;

said frame including a web interposed between said base and said connection means, said cover being movable relative to said base by flexing of said web while said joint between said cover and frame is maintained, said web forming a portion of said enclosed space, said web flexing not being permanent, said web being bendable relative to said base to permit said cover to move relative to said base.

2. A protective covering as in claim 1, wherein said connection means includes a wall connected at one end to said web and extending away from said base, said cover including contact means for engaging said wall, said cover being releasable from said frame wall.

3. A protective covering as in claim 2, wherein said web has length and is one of wavy, linear and arcuate along said length.

4. A protective covering as in claim 3, wherein said web has thickness, said length being greater than said thickness.

5. A protective covering as in claim 2, wherein said cover is an elastic cup that snaps around said wall of said connection means on said frame, said elastic cup applying a compressive force on said frame to maintain connection between said cover and frame.

6. A protective covering as in claim 2, wherein said cover is a flexible sheet, said sheet being maintained in connection with said wall on said frame, said cover being connected to said frame by a compressive force, and further comprising means for applying said compressive force.

7. A protective covering as in claim 2, wherein said wall has a protrusion extending radially outward at a second end.

8. A protective covering as in claim 1, wherein said web has length and is one of wavy, linear and arcuate along said length.

9. A protective covering as in claim 8, wherein said web has thickness, said length being greater than said thickness.

10. A protective covering as in claim 1, wherein said cover is at least one of flexible and elastic material.

11. A protective covering as in claim 1, wherein said enclosed space is one of sealed and unsealed relative to external ambient environment.

12. A protective covering as in claim 1, wherein said cover is an elastic cup that snaps around a periphery of said connection means on said frame, said elastic cup applying a compressive force on said frame to maintain connection between said cover and frame.

13. A protective covering as in claim 1, wherein said cover is a flexible sheet, said sheet being maintained in connection with a periphery of said connection means on said frame, said cover being connected to said frame by a compressive force, and further comprising means for applying said compressive force.

14. A protective covering as in claim 1, wherein said base is at least one of generally planar and curved.

15. A protective cover for a body lesion of a patient comprising:

a frame having a base with a base surface, said base surface having adhesive means for maintaining said frame in sealed contact with a body surface of said patient, said frame defining an opening for surrounding said lesion;

connection means on said frame for connecting to a cover for covering said frame opening; and a flexible web interposed between said base and said connection means, to permit movement relative to said base by flexing of said web, said web flexing not being permanent, said web being bendable relative to said base to permit said connection means to move relative to said base.

16. A protective covering as in claim 15, wherein said connection means includes a wall connected at one end to said web and extending away from said base.

17. A protective covering as in claim 16, wherein said wall has a protrusion extending radially outward at a second end.

18. A protective covering as in claim 15, wherein said web has length and is one of wavy, linear, and arcuate along said length.

* * * * *